(12) United States Patent
Marar

(10) Patent No.: US 7,519,156 B2
(45) Date of Patent: Apr. 14, 2009

(54) METHOD AND APPARATUS FOR HOT SWAPPING PORTABLE DETECTORS IN X-RAY SYSTEMS

(75) Inventor: Rajeev R. Marar, Waukesha, WI (US)

(73) Assignee: General Electric Company, Schenectady, NY (US)

(*) Notice: Subject to any disclaimer, the term of this patent is extended or adjusted under 35 U.S.C. 154(b) by 154 days.

(21) Appl. No.: 11/752,793

(22) Filed: May 23, 2007

(65) Prior Publication Data

US 2008/0292062 A1 Nov. 27, 2008

(51) Int. Cl.
H05G 1/54 (2006.01)
G01D 18/00 (2006.01)
(52) U.S. Cl. .................... 378/116; 378/207
(58) Field of Classification Search ............ 378/116, 378/207, 189, 197, 193, 198
See application file for complete search history.

(56) References Cited

U.S. PATENT DOCUMENTS

| | | | |
|---|---|---|---|
| 6,702,459 B2 * | 3/2004 | Barnes et al. | 378/197 |
| 2002/0150214 A1 * | 10/2002 | Spahn | 378/189 |
| 2002/0176535 A1 * | 11/2002 | Dixon et al. | 378/62 |
| 2003/0058998 A1 * | 3/2003 | Aufrichtig et al. | 378/207 |

* cited by examiner

Primary Examiner—Irakli Kiknadze
(74) Attorney, Agent, or Firm—Peter Vogel, Esq.; William Baxter, Esq.; Michael G. Smith, Esq.

(57) ABSTRACT

Methods and apparatus are provided for hot swapping a portable detector to an imaging system. A portable detector having a unique identifier and calibration data is detected by an imaging system. The imaging system selects the calibration data for the detected portable detector. The imaging system uses the calibration data in the imaging process. In some embodiments, the selected calibration data can be stored in the portable detector or in the imaging system. In some embodiments, the calibration data is organized as both imaging system dependent and imaging system independent. In some embodiments, the imaging system integrates the portable detector and the associated calibration data into the operation of the imaging system.

20 Claims, 12 Drawing Sheets

METHOD AND APPARATUS FOR HOT SWAPPING PORTABLE DETECTORS IN X-RAY SYSTEMS

FIELD OF THE INVENTION

The present invention relates generally to diagnostic imaging and, more particularly, to the integration of a portable detector to an imaging system.

BACKGROUND OF THE INVENTION

X-ray imaging is a non-invasive technique to capture images of medical patients for clinical diagnosis as well as inspect the contents of sealed containers, such as luggage, packages, and other parcels. To capture these images, an X-ray source irradiates a scan subject with a fan beam of X-rays. The X-rays are then attenuated as the X-rays pass through the scan subject. The degree of attenuation varies across the scan subject because of variances in the internal composition of the subject. The attenuated energy impinges upon an X-ray detector designed to convert the attenuating energy to a form usable in image reconstruction. A control system reads out electrical charge stored in the X-ray detector and generates a corresponding image. For a conventional, screen film detector, the image is developed on a film and displayed using a backlight.

Increasingly, flat panel, digital X-ray detectors are being used to acquire data for image reconstruction. Flat panel detectors are generally constructed as having a scintillator which is used to convert X-rays to visible light that can be detected by a photosensitive layer. The photosensitive layer includes an array of photosensitive or detector elements that each store electrical charge in proportion to the light that is individually detected. Generally, each detector element has a light sensitive region and a region comprised of electronics to control the storage and output of electrical charge. The light sensitive region is typically composed of a photoconductor, and electrons are released in the photoconductor when exposed to visible light. During this exposure, charge is collected in each detector element and is stored in a capacitor situated in the electronics region. After exposure, the charge in each detector element is read out using logic controlled electronics.

In order to maintain optimum image quality, frequent calibration of the digital X-ray detectors and the imaging system (host) is encouraged. However, this requires user intervention, to generate the X-rays at a time when there is nothing "in the beam" in front of the detector. During calibration, the system is not available for use, resulting in loss of productivity of the X-ray system. For digital X-ray detectors that can be used with more than one imaging system the calibration becomes even more complex. To further add to the complexity digital detectors are likely to be wireless and require battery support.

In a typical world of fixed detectors, a system (RAD/RF or Portable) is be calibrated only for one detector or one set of detectors. Also each of the detectors is calibrated with only one system in mind. This is a one to one arrangement.

But with wireless or detachable detectors, the systems primarily support a common interface to attach detectors such as Ethernet/wireless or Ethernet with power combination and the relationship becomes a one to many. That is, a detector can be used with any system that with which the detector can communicate with. If the workflow and design of the systems is similar to the current fixed detector systems (one to one), an operator can try to use a detector that is calibrated for another system, leading to a reduction in the quality of the images and in a reduction in the workflow for that operator. Further, note that the same reduction in workflow is possible when employing multiple mobile systems using wireless detectors. Failures are detected only very late in the workflow and failure will cause significant delay of service to find and use the correct detector for the system.

For the reasons stated above, and for other reasons stated below which will become apparent to those skilled in the art upon reading and understanding the present specification, there is a need in the art for providing an imaging system with access to calibration information for any detector. There is also a need for improved integration of wireless or detachable detectors to an imaging system.

BRIEF DESCRIPTION OF THE INVENTION

The above-mentioned shortcomings, disadvantages and problems are addressed herein, which will be understood by reading and studying the following specification.

In one aspect, a portable detector having a unique identifier is detected by an imaging system. The imaging system then selects the calibration data for the detected portable detector. The selected calibration data can be stored in the portable detector or in the imaging system. The calibration data is organized as both imaging system dependent and imaging system independent. The imaging system integrates the portable detector and the associated calibration data into the operation of the imaging system.

In another aspect, the portable detector's unique identifier is a marker added to the portable detector at the time of calibration, or an identifier such as a serial number in the portable detector's firmware, or a media access control access assigned to the portable detector by a network appliance.

In yet another aspect, a system having a processor, storage device couple to the processor, and software means for integrating a portable detector to an imaging system with the calibration data for the portable detector, In still another aspect, a computer accessible medium having executable instructions for integrating a portable detector to an imaging system by directing a processor to detect attachment of a portable detector to the imaging system, exchange communications with the portable detector, and select based on the communication the calibration data for the portable detector.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific embodiments which can be practiced. These embodiments are described in sufficient detail to enable those skilled in the art to practice the embodiments, and it is to be understood that other embodiments can be utilized and that logical, mechanical, electrical and other changes can be made without departing from the scope of the embodiments. The following detailed description is, therefore, not to be taken in a limiting sense.

Figure 1:
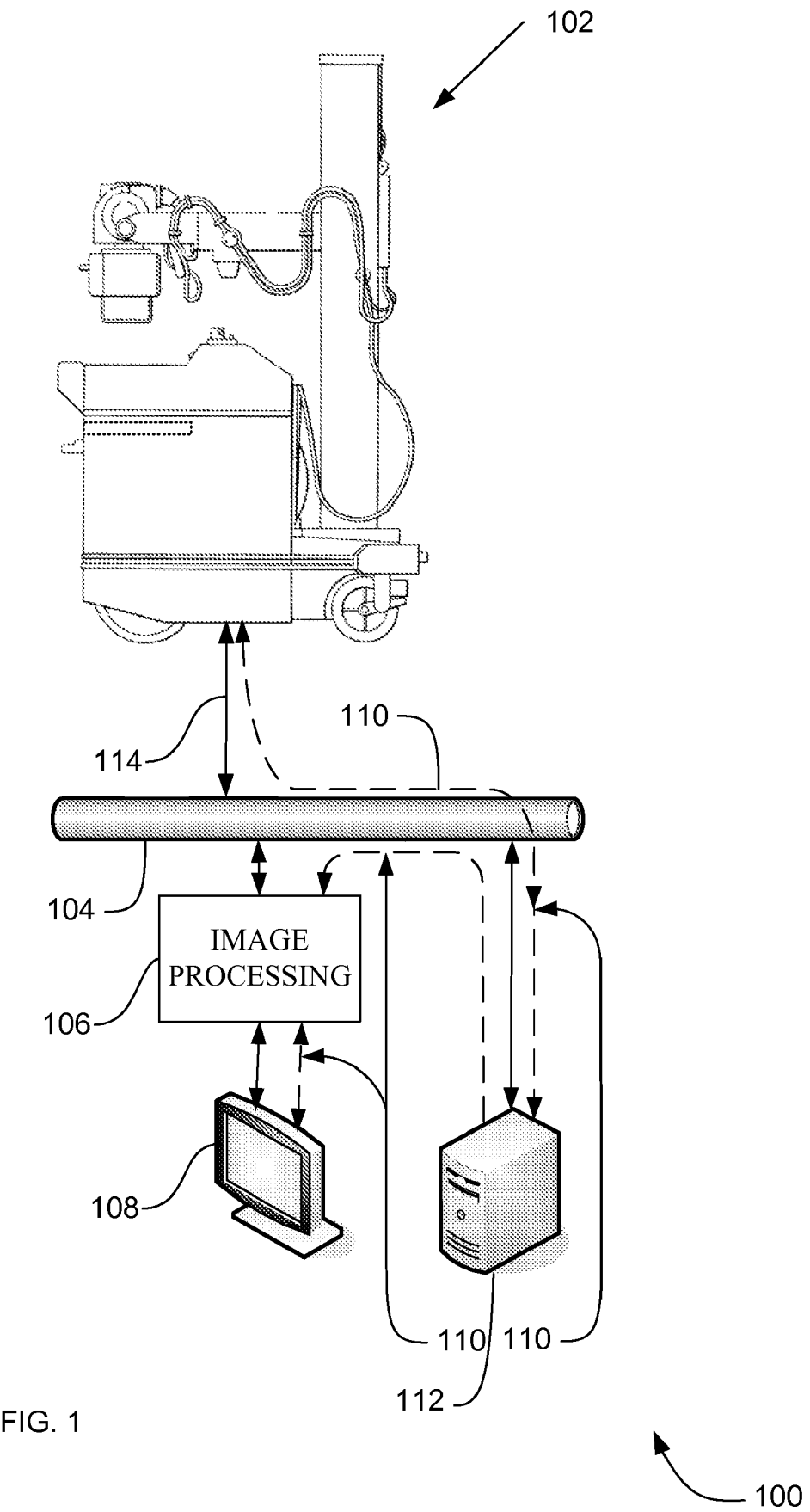
FIG. 1 is a block diagram of a network connected mobile medical digital X-ray imaging system according to an embodiment.

FIG. 1 is a block diagram that provides an overview of a system to capture a digital image at a mobile medical digital X-ray imaging system 102 and for processing the digital image in a network environment. System 100 solves the need in the art for an imaging system with access to calibration information for any detector.

System 100 includes a mobile digital imaging system 102, such as the mobile X-ray digital imaging system shown in FIG. 1. The mobile digital imaging system 102 is operably coupled to a network 104, such as an Ethernet compliant network shown in FIG. 1. In some embodiments, the network is a network that is specifically adapted to function as a medical imaging network.

System 100 also includes an image processing system 106 with display device 108.

The X-ray system preferably has a mechanism to hold a portable digital detector until the portable digital detector is needed by the operator, user, or X-ray technician. This mechanism can also serve as a supply and/or communication center through an IT interface device. The IT interface device is a link point for the efficient transmission of recorded image data from the mobile digital radiography system 102. The IT interface can be a wireless link, an electrical link, or an optoelectronic link.

After the mobile imaging system 102 captures a digital image, the digital image can be optionally transmitted to the network 104 along communication path 110. A server 112 on the network 104 receives the digital image and transmits the digital image along communication path 110 to an image processing system such as image processing system 106 having display device 108 for displaying the digital image in real time permitting instant review by a trained operator in a control room.

A coupling 114 between the mobile digital imaging system 102 and the network can be accomplished in one of a number of means. For example, a wireless connection is implemented between the mobile digital imaging system 102 and the network. In some embodiments, a wired connection is implemented. In some embodiments, and coupling 114 includes the Internet.

While the system 100 is not limited to any particular mobile digital imaging system 102, network 104, image processing system 106, display device 108, communication path 110, server 112, or coupling 114, for sake of clarity a simplified mobile digital imaging system 102, network 104, image processing system 106, display device 108, communication path 110, server 112, and coupling 114 are described.

Figure 2:
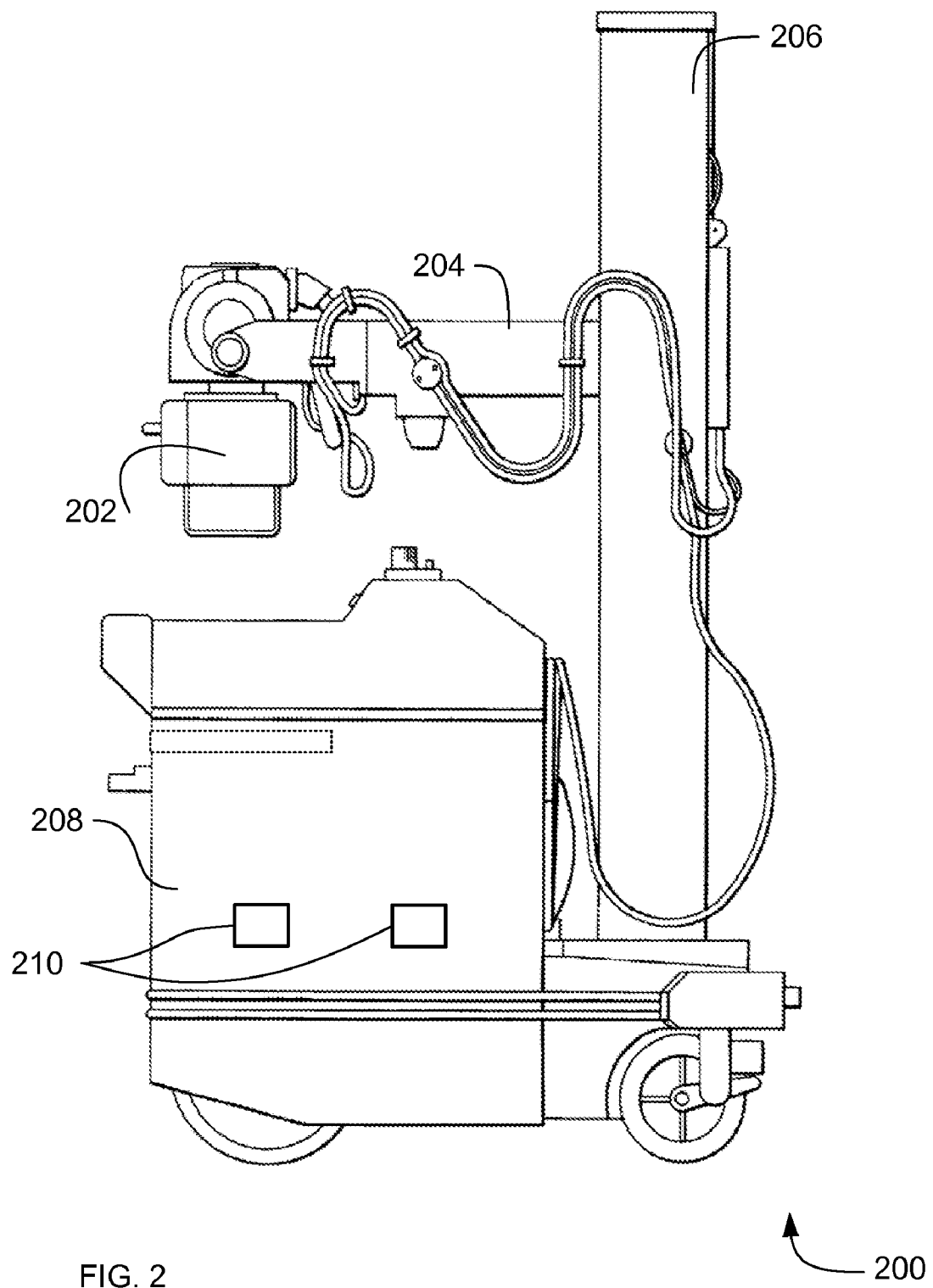
FIG. 2 is a side view of mobile digital X-ray imaging system according to an embodiment having a plurality of network interfaces.

FIG. 2 is a side view of mobile digital X-ray imaging system 200 according to an embodiment having a plurality of network interfaces. Mobile digital X-ray imaging system 200 includes an X-ray source 202 mounted at the end of horizontal arm 204. The X-ray source 202 is positionable over the object or region of interest to be imaged. The X-ray source 202 is typically mounted through a gimbal type arrangement in which a column 206 is required to rotate to move the X-ray source from the park position on the mobile X-ray unit base 208 to the appropriate position in order to take an X-ray image of the patient.

Mobile digital X-ray imaging system 200 also includes a plurality of network adapters 210. Two network adapters in the plurality of network adaptors 210 are shown in FIG. 2, but any number of network adapters more than one can be implemented. The network adapters 210 can be used to connect to an external digital X-ray detector and as an interface to an electronic system that is operable to display an image from the mobile digital X-ray imaging system 200, such as system 100. At least one of the network adapters 210 is a conventional network adapter, such as an Ethernet adapter.

The graphical depiction of the size of the network adapters 210 is increased relative to the mobile digital X-ray imaging system 200 in FIG. 2 in order to improve legibility of the network adapters 210. The actual network adapters are usually smaller in size relative to the mobile digital X-ray imaging system 200.

In an alternative embodiment, mobile digital X-ray imaging system 200 includes only one network adapter to communicate to the electronic system that is operable to display an image from the mobile digital X-ray imaging system 200, such as system 100.

The network adapters 210 are Ethernet network adapters allowing the mobile digital imaging systems to exchange files, to share resources, and to propagate calibration data. In some embodiments, the Ethernet compliant communication channel couples to a router, that in turn in coupled to the Internet, that in turn is connected to a network, such as network 104 in FIG. 1 that provides display and processing apparatus and capability on a digital image that is captured by the mobile digital imaging system 102. In some embodiments, the Ethernet compliant communication channel is a direct wired connection to the network, such as network 104 in FIG. 1. As an alternative to Ethernet, other conventional network protocols can be used, such as LocalTalk that was developed by Apple Computer, Inc., token ring protocol that was developed by IBM, fiber distributed data interface (FDDI), and asynchronous transfer mode (ATM). In addition, any conventional network topology can be used, such as linear bus, star, tree, star-wired ring or dual ring.

Mobile digital X-ray imaging system 200 shows a network adaptor for a wired Ethernet connector. However mediums other than wires can be implemented, such as wireless connection (e.g. infrared or radio) to couple or connect the mobile digital X-ray imaging system 200 to a network.

Figure 3:
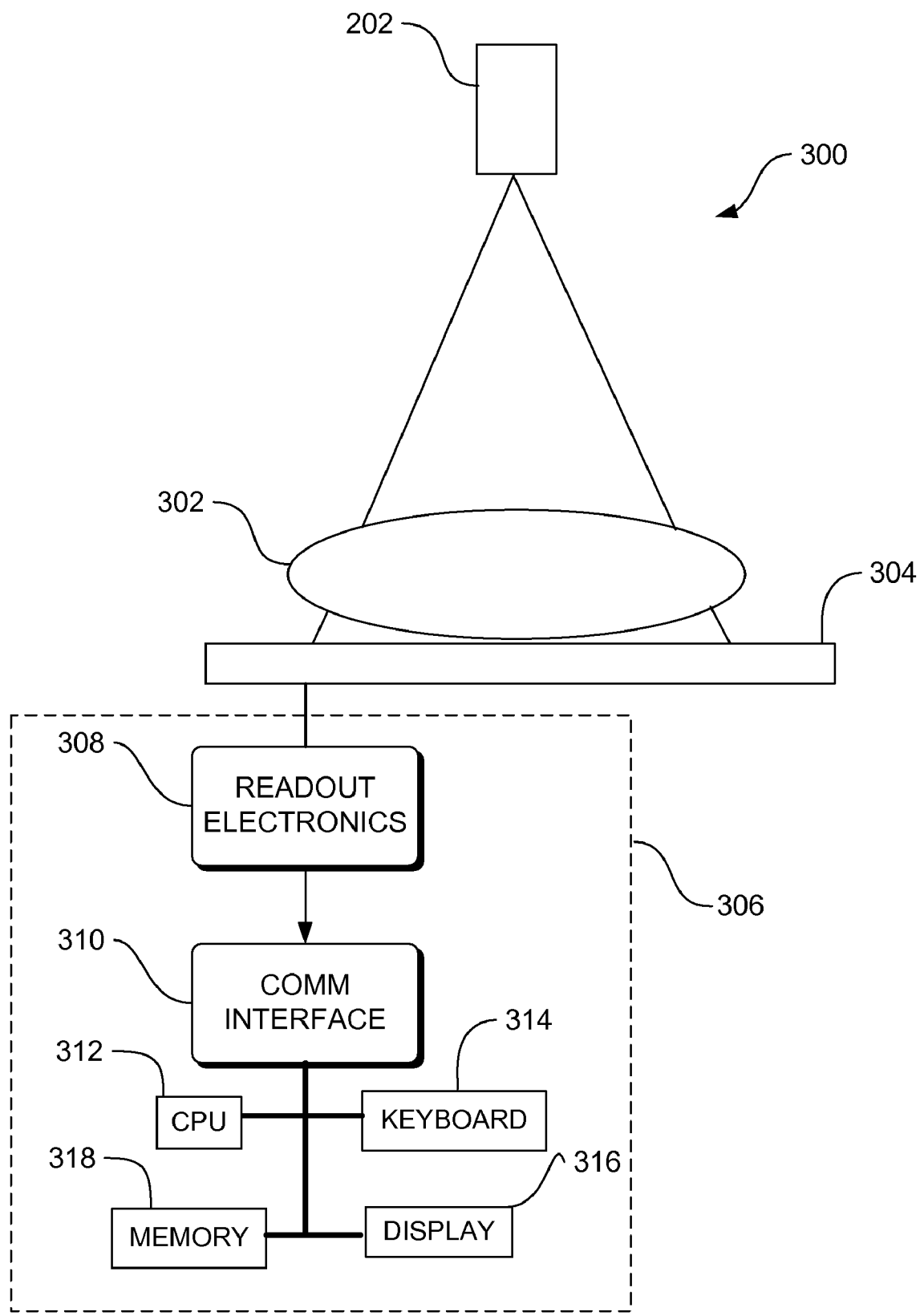
FIG. 3 is a schematic block diagram of an exemplary X-ray imaging system.

Referring now to FIG. 3, a schematic of X-ray imaging system 300 is illustrated. As referenced above, system 300 includes X-ray source 202 designed to project a fan bean of irradiation from focal spot along axis toward an object to be imaged 302. One skilled in the art will appreciate that medical patients as well as luggage, packages, and the like can be non-invasively inspected using the exemplary X-ray imaging system 300. A flat panel digital detector 304 detects X-rays passing through and attenuated by object 302. A collimator assembly (not shown comprising collimator blades, can be used to collimate the X-ray fan beam to control the scope of irradiation.

A host or scanner interface 306 includes a communication interface 310, a keyboard 314 or other data entry device, a CPU 312, memory 318, and a display unit 316, such a computer monitor, to display reconstructed images of the object. A bus connects the keyboard 314, CPU 312, memory 318, and display unit 316 to the communication interface 310. The CPU can include a microprocessor, digital signal processor, microcontroller, as well as other devices designed to carry out logic and processing operations. Signals corresponding to an X-ray image are read out from flat panel detector 304 via readout electronics 308. While not shown, the host interface 308 is contemplated as operable to be connected to a centralized facility via the Internet or communications link for monitoring and maintenance as shown in FIG. 1.

Computer or CPU 312 also includes an operating system (not shown) that is stored on the computer-accessible media RAM, ROM, and mass storage device, and is executed by processor. Examples of operating systems include Microsoft Windows®, Apple MacOS®, Linux®, UNIX®. Examples are not limited to any particular operating system, however, and the construction and use of such operating systems are well known within the art.

Embodiments of computer 312 are not limited to any type of computer. In varying embodiments, computer 312 comprises a PC-compatible computer, a MacOS®-compatible computer, a Linux®-compatible computer, or a UNIX®-compatible computer. The construction and operation of such computers are well known within the art.

Computer 302 can be operated using at least one operating system to provide a graphical user interface (GUI) including a user-controllable pointer. Computer 302 can have at least one web browser application program executing within at least one operating system, to permit users of computer 302 to access an intranet, extranet or Internet world-wide-web pages as addressed by Universal Resource Locator (URL) addresses. Examples of browser application programs include Netscape Navigator® and Microsoft Internet Explorer®.

Additionally, the readout electronics can read out signals from the flat panel detector across a tethered connection between the detector and the imaging system. It is also contemplated that read out can be achieved across a wireless communication between the detector and imaging system. In this regard, one skilled in the art will appreciate that the imaging system and detector can be equipped with transceivers, antennas, and other operational circuitry to support the wireless transmission of data.

Figure 4:
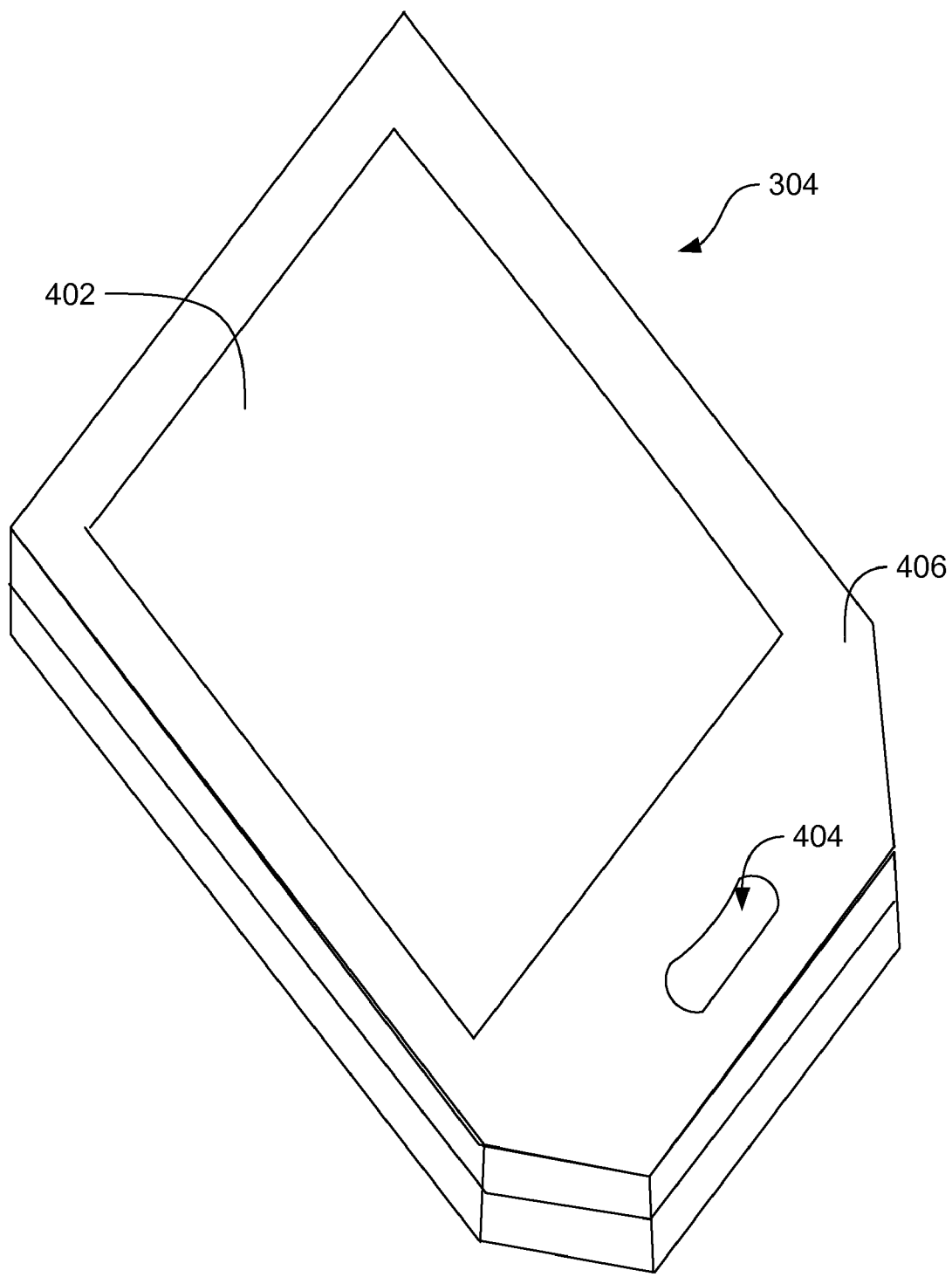
FIG. 4 is a perspective view of a portable, solid-state, flat panel, digital X-ray detector incorporating the present invention.

FIG. 4 is a perspective view illustrates a portable, flat panel X-ray detector 304 incorporating the present invention. Detector 304 is preferably an indirect detection, solid-state, digital detector that determines X-ray attenuation through an imaging subject from the emission of light by a scintillator that emits light upon the incidence of X-rays. The detector 304 includes a cover 406 formed of lightweight, durable composite material. A handle 404 is incorporated into the cover to support the portability of the detector. As shown, the detector 304 can be constructed without a fixed tether. In this regard, the detector can be connected to a tether (not shown), which is connected to the readout electronics when in use. When not in use, the detector can be easily detached from tether and stored remotely from the imaging system. The top of the cover includes a template 402 that visually defines the surface dimensions of the scintillator layer in the detector. Template 402 is designed to visually assist a user in positioning of the detector for data acquisition.

While the present invention is particularly applicable with indirect detection digital detectors, the present invention can also be implemented with direct detection digital detectors. Direct detection digital detectors utilize a layer of amorphous selenium or similar material photoconductor coupled to a thin film transistor array. X-ray interaction in the selenium layer releases electrons (or electron holes), which are used to form signal directly. An electrode is often used to create an electric field across the selenium layer to minimize the lateral spread of electrons, preserving spatial resolution. In addition to selenium, mercuric iodide, cadmium telluride, and lead iodide can be used.

Figure 5:
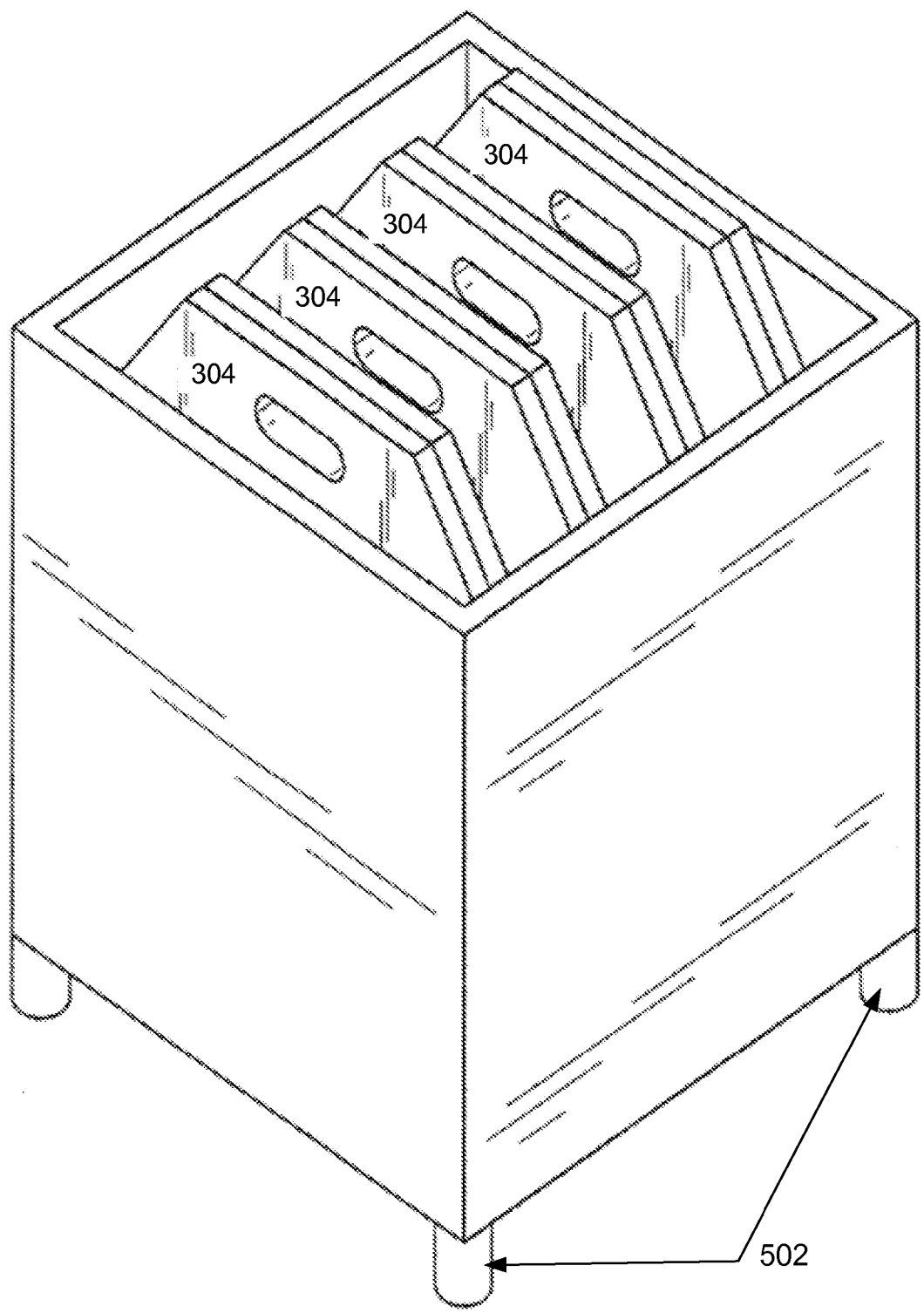
FIG. 5 is perspective view of an X-ray detector docking station according to an embodiment.

FIG. 5 is a docking station 500 for an X-ray detector is shown. The docking station 500 illustrated is sized to store multiple X-ray detectors 304; however, in come embodiments, the docking station holds a single X-ray detector. Docking station 500 can be free-standing and, as such, include legs 502 or mounted on a wall or other structure (not shown) in a customary manner. The docking station is a dual purpose apparatus as the docking station 500 is designed to store X-ray detectors while the X-ray detectors are not in use, and includes a thermal exchanger and control to regulate the temperature of the stored X-ray detectors. As described below in detail, in some embodiments the thermal regulation of stored X-ray detectors can be achieved in accordance with the principles of radiation, conduction, convection, or a combination thereof.

Figure 6:
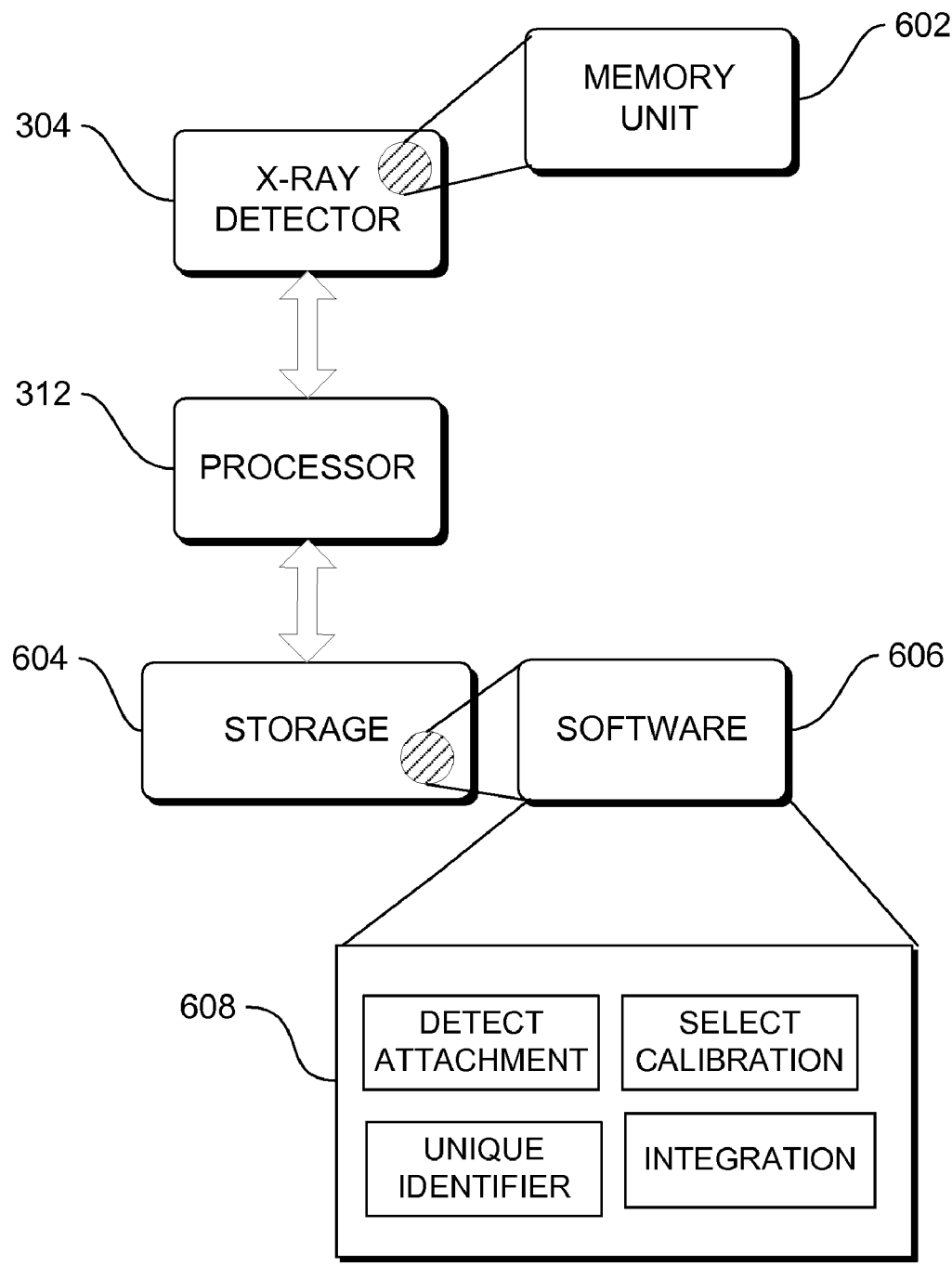
FIG. 6 is a block diagram of a hardware and operating environment in which different embodiments can be practiced.

FIG. 6 illustrates a system overview of a system 600 for integrating a portable detector to an imaging system. System 600 comprises an X-ray detector 304, processor 312, a memory unit 602 at the X-ray detector, a storage device 604, and software component 606 having objects 608 for performing the functions of detecting when the portable detector is attached, selecting calibration data, assigning or reading a unique identifier, and integrating the portable detector to the imaging system. Memory unit 602 can include a one or more cache, ROM, PROM, EPROM, EEPROM, flash, SRAM, non-volatile memory (NVM), or other devices; however, the memory is not limited thereto. Memory unit can hold calibration data, a unique identifier assigned to the detector by the calibration host, a serial number assigned at the factory, or a media access control address. Since each detector 304 contains its own calibration data, hot swapping the detector into the imaging process produces improvements in down time. This easy replacement of the detector 304 makes the process much quicker. No new calibration is required when the detector 304 is replaced. All the settings, including the calibration, are stored within the detector 304 for easy access. The memory 602 of each detector would have the calibration data for all the systems of a given area or designation. The portion of the detector's memory (NVM) for the independent calibration data would be arranged as follows:

Detector calibration data for system 1.

Detector calibration data for system 2.

Detector calibration data for system 3.

⋮

Detector Calibration data for system N.

In FIGS. 1-5, a system level overview of the operation of an embodiment is described. In this section, the particular methods of such an embodiment are described by reference to a series of flowcharts. Describing the methods by reference to a flowchart enables one skilled in the art to develop such programs, firmware, or hardware, including such instructions to carry out the methods on suitable computers, executing the instructions from computer-readable media. Similarly, the methods performed by the server computer programs, firmware, or hardware are also composed of computer-executable instructions. Methods 700-1000 are performed by a program executing on, or performed by firmware or hardware that is a part of, a computer, such as computer 312 in FIG. 3

Figure 7:
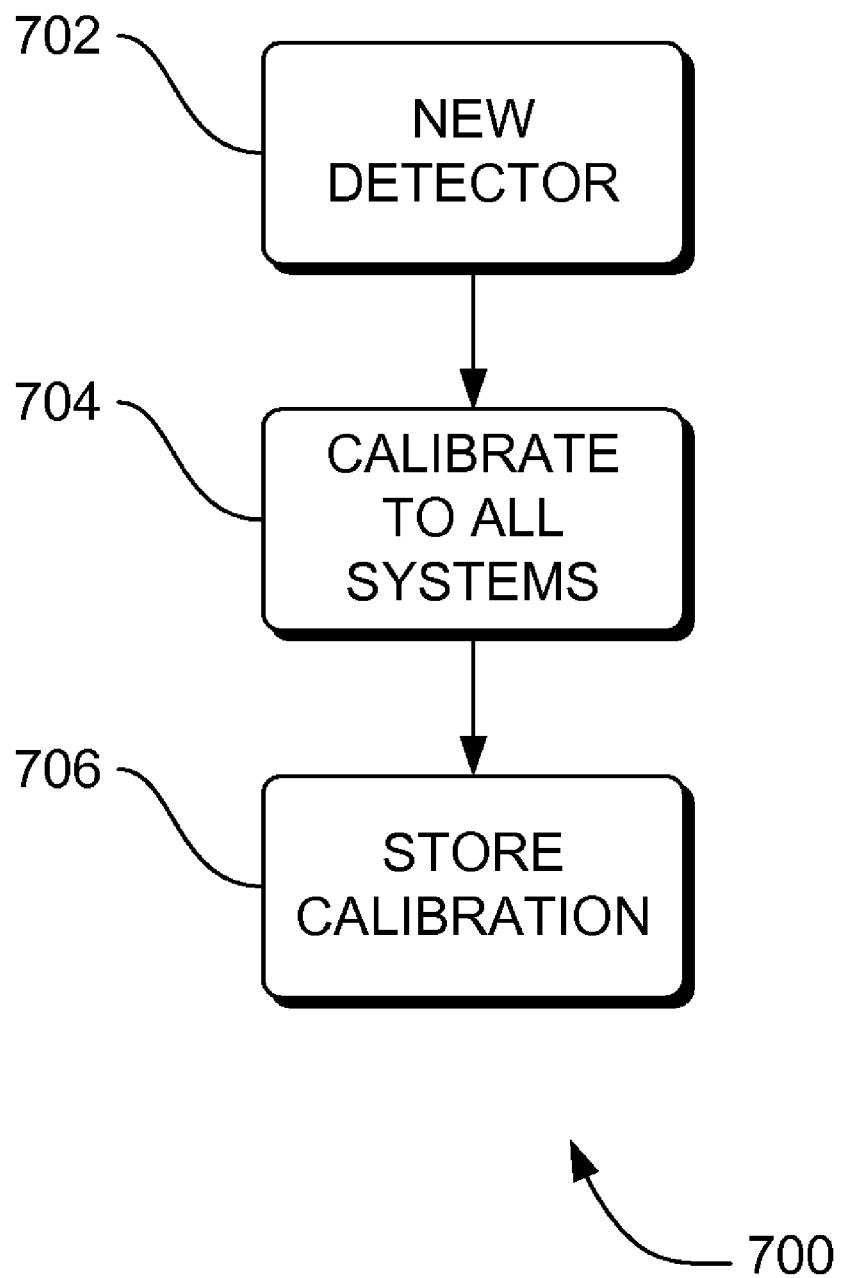
FIG. 7 is a flowchart of a method for calibrating a new detector, according to an embodiment.

FIG. 7 is a flowchart of a method 700 for calibrating a new portable detector, according to an embodiment. Method 700 solves the need in the art to for providing an imaging system with access to calibration information for any detector that needs to be used.

Method 700 includes action 702 for recognizing a new detector, action 704 for performing a calibration, and action 706 for storing the calibration of the new detector.

In action a 702 new detector is recognized. At this point the unique identifier such as serial number is read by the calibration host. In the alternative when an internal or institutional identifier is preferred the host assigns such an identifier to the new detector. In yet another alternative, a MAC address is assigned to the new detector. Regardless of the identifier selected or assigned the new detector is know by that designation and can be tracked through the network.

In action 704 the new detector is calibrated for all systems. The calibration procedure is administered and the new detector is calibrated for imaging applications such as bad pixel, gain, etcetera. However, since detector is operable with different systems the detector is calibrated to all known system that can use the detector.

In action 706 the calibration information is store. In a network environment there are a myriad of places where the calibration information can be stored. For example, the calibration can be stored in the detector such as portable detector 304 and every time the detector is used by an imaging system the detector can incorporate the calibration data in the imaging operation. In the alternative, the calibration data can be propagated to all the imaging systems. When a detector is coupled to an imaging system all the host has to do is select the calibration data for the detector from its internal memory. The calibration data can index based on the unique identifier of the respective portable detector.

Figure 8:
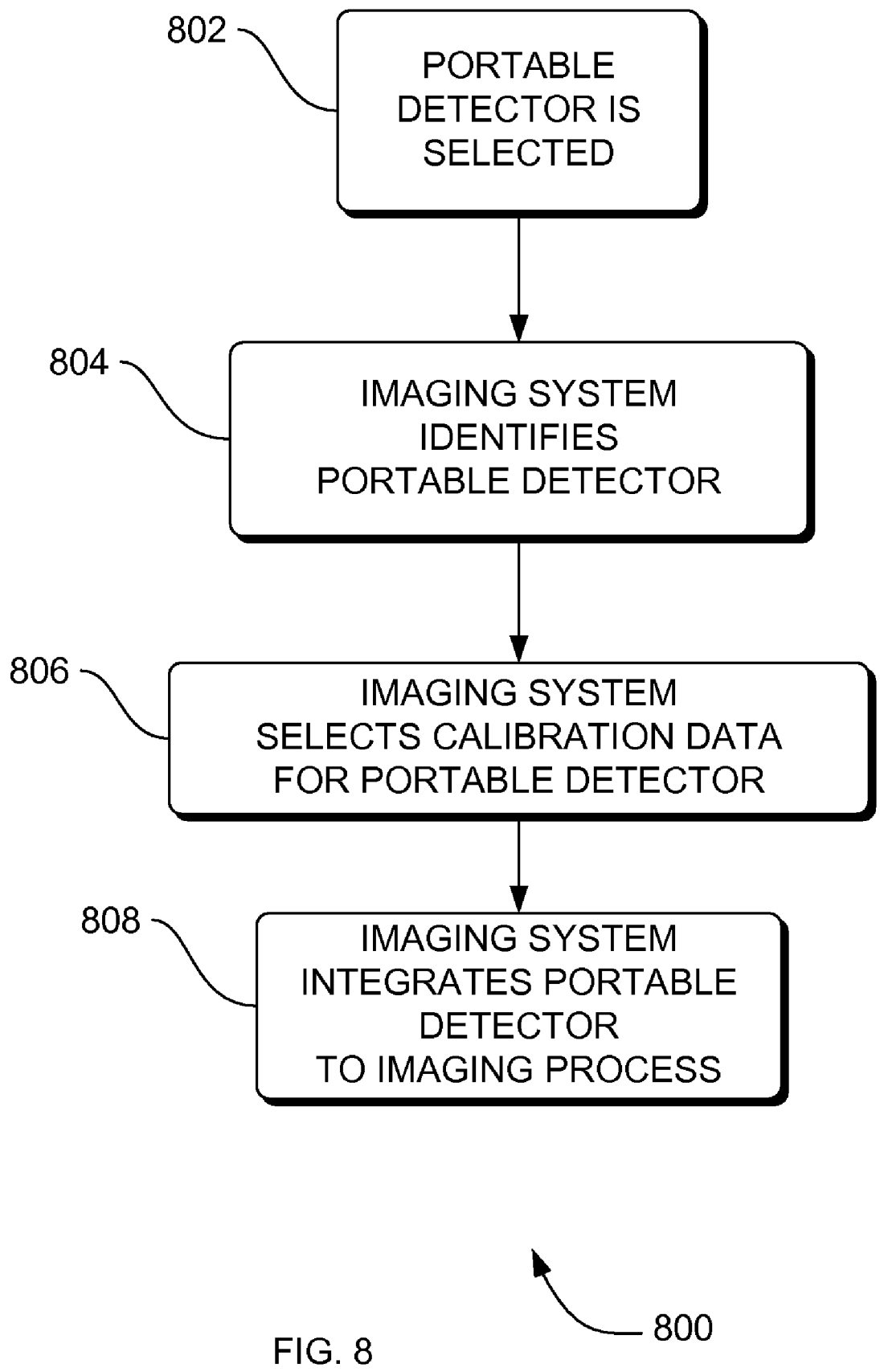
FIG. 8 is a flowchart of a method for integrating a portable detector with an imaging system, according to an embodiment.

FIG. 8 is a flowchart of a method 800 of integrating a portable detector to an imaging system, according to an embodiment. Method 800 follows the procedure for hot swapping the detector 304 to the imaging system 100 in the event that the detector 304 is not functioning within tolerances. A detector 304 may be out of tolerance when the battery is below a certain kevel, when the temperature exceeds a threshold, or when the detector fails to operate within acceptable levels. The terms hot swap, hot insertion, or plug-and-play are conveniently used to refer to the exchange or insertion of portable detectors 304 into the imaging process so as to allow the imaging system 100 to function immediately after the swapping or insertion process takes place. Method 800 solves the need in the art for easy integration of portable detectors through calibration data sharing.

Method 800 includes selecting a portable detector 802, identification of the portable detector 804, selecting the calibration data 806, and integrating the portable detector to the imaging process 808.

In action 802 a portable detector is selected. The portable detector is any detector capable of exchanging information with the imaging system using a well defined protocol such as docking protocol or wireless protocol.

In action 804 the host or imaging system identifies the detector using the defined protocol. The system then proceeds to read the identification and the calibration data from the detector. In the alternative, the host can look up the stored calibration data for the given detector. The unique identifier of the detector can be used as the index key of the table for reading the calibration data.

In action 806, the calibration data is selected for the portable detector. The calibration data is unique for that detector.

In action 808, the imaging system uses the calibration data to integrate the detector to the imaging process of the imaging system.

Figure 9:
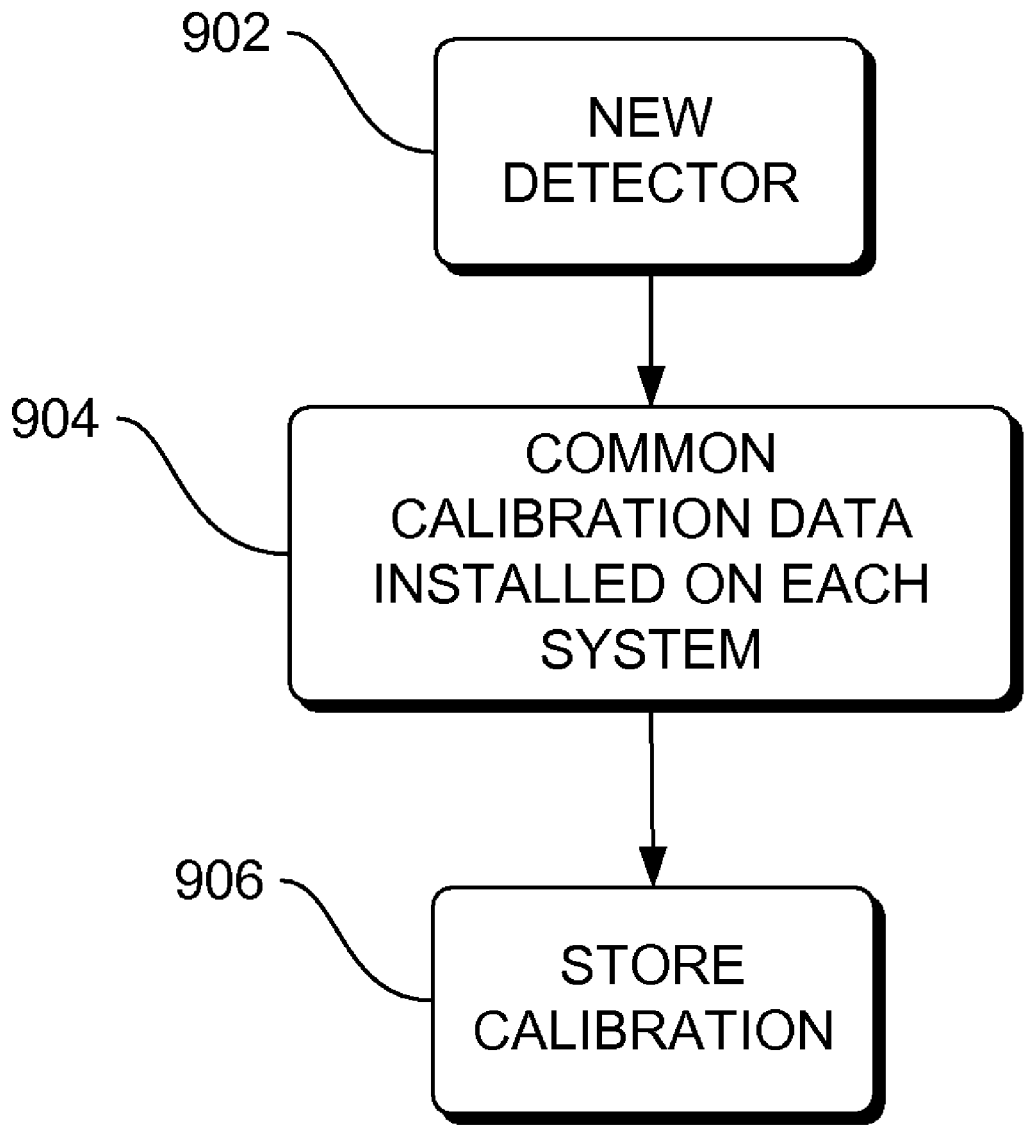
FIG. 9 is a flowchart of a method for propagating in all imaging system common calibration data for a new detector, according to an embodiment.

FIG. 9 is a flowchart of a method 900 for calibrating a new portable detector, according to an embodiment. Method 900 solves the need in the art for providing an imaging system with access to calibration information for any detector that needs to be used.

Method 900 includes action 902 for recognizing a new detector, action 904 for performing a calibration and for propagating the information to all systems, and action 906 for storing the calibration of the new detector.

In action a 902 new detector is recognized. At this point the unique identifier such as serial number is read by the calibration host. In the alternative when an internal or institutional identifier is preferred the host assigns such an identifier to the new detector. In yet another alternative, a MAC address can be assigned to the new detector. Regardless of the identifier selected or assigned the new detector is know by that designation and can be tracked through the network.

In action 904 the new detector is calibrated for all systems. The calibration procedure is administered and the new detector is calibrated for imaging applications such as bad pixel, gain, etcetera. The detector is calibrated to all known system that can use the detector. The calibration data for the detector is propagated to all imaging systems for storing for later use with the new detector. The propagation of the calibration data enables the imaging system to quickly identify those calibration parameters for the portable detector. When a detector is coupled to an imaging system all the host has to do is select the calibration data for the detector from its internal memory. The calibration data can be index based on the unique identifier of the respective portable detector.

In action 906 the calibration information is store. In a network environment there are a myriad of places where the calibration information can be stored. For example, the calibration can be stored in the detector such as portable detector 304 and every time the detector is used by an imaging system the detector can incorporate the calibration data in the imaging operation.

Figure 10:
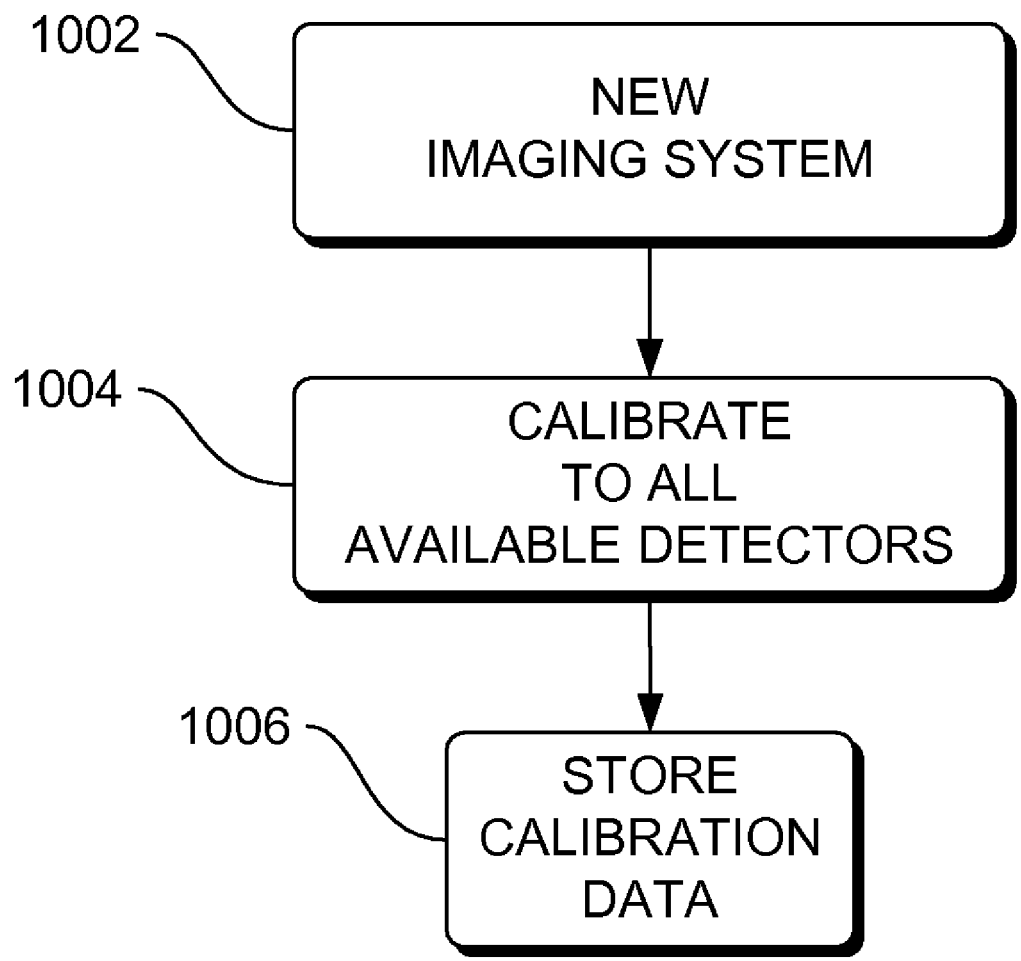
FIG. 10 is a flowchart of a method for calibrating a new imaging system, according to an embodiment.

FIG. 10 is a flowchart of a method 1000 for integrating a portable detector to an imaging system, according to an embodiment. Method 1000 solves the need in the art for providing an imaging system with access to calibration information for any detector that needs to be used.

Method 1000 includes identification of a new imaging system 1002, calibration of the system to all detectors 1004, and storing of the calibration data.

In action 1002, a new imaging system is identified. The imaging system as noted earlier can be a RAD and RF system for taking digital RAD exposures.

In action 1004, the imaging system is calculated for all available detectors. The calibration procedure is administered and the new imaging is calibrated for imaging applications such as bad pixel, gain, etc. The system is calibrated to all known detectors that can use the system.

In action 1008, the calibration data either is stored in the system or is made available to other devices connected to the network that can have a need for the data.

In some embodiments, methods 700-1000 are implemented as a computer data signal embodied in a carrier wave, that represents a sequence of instructions which, when executed by a processor, such as processor 312 in FIG. 6, cause the processor to perform the respective method. In other embodiments, methods 200-1000 are implemented as a computer-accessible medium having executable instructions capable of directing a processor, such as processor 312 in FIG. 6, to perform the respective method. In varying embodiments, the medium is a magnetic medium, an electronic medium, or an optical medium.

Figure 11:
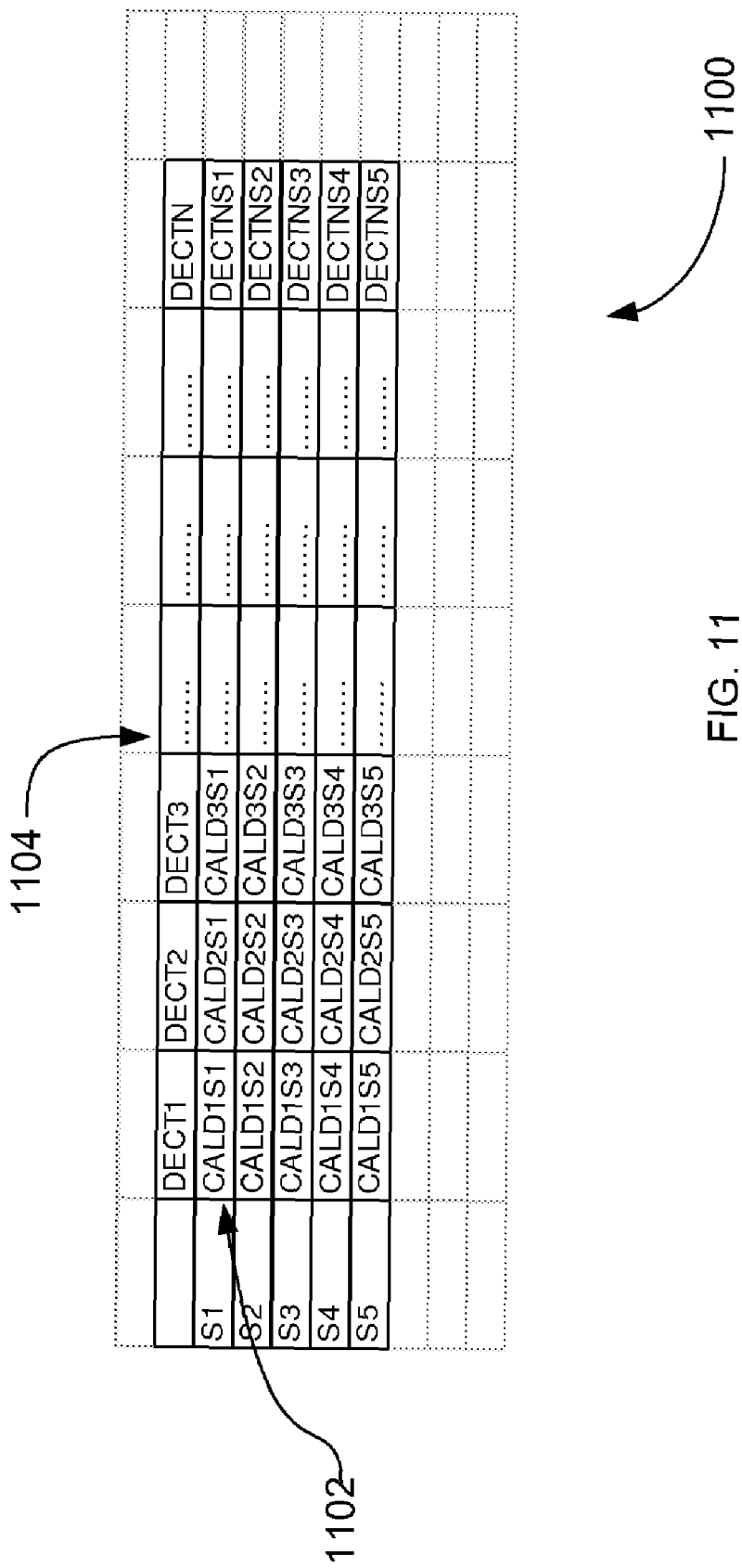
FIG. 11 is a table illustrating the relationship of the imaging system, portable detectors, and calibration data according to an embodiment.

FIG. 11 is an illustration of table 1100 showing row of imaging systems (S1 . . . S5) and column detectors (DECT1 . . . DECT7). For example, calibration data three (CALDNS1) corresponds to the calibration data for detector N and imaging system 1 (S1). Each detector would have the calibration data for all systems on which the detector may be used. A master table can be stored in server 112 (FIG. 1) for later retrieval.

Figure 12:
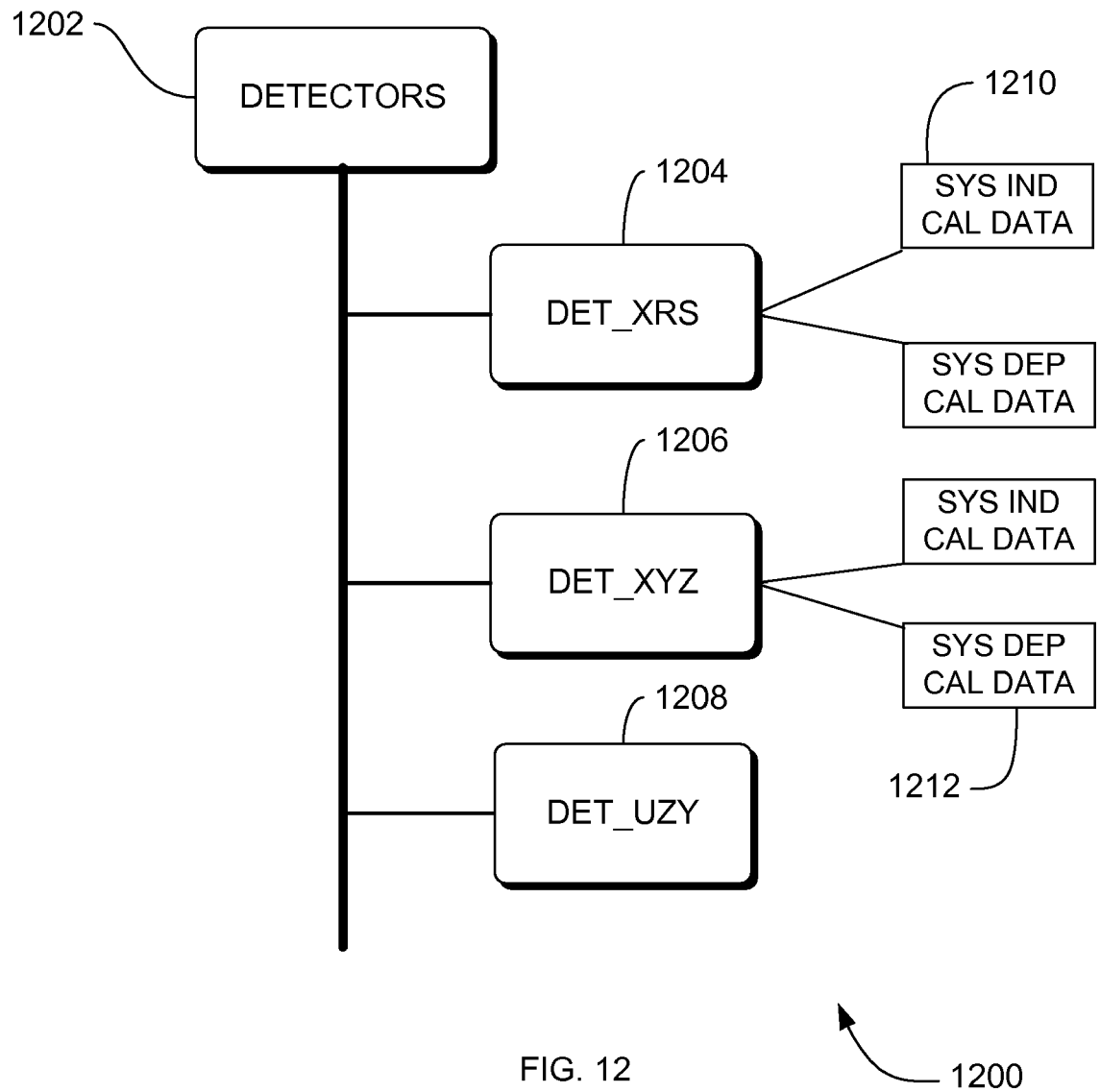
FIG. 12 is a diagram of a data structure for use in an implementation.

FIG. 12 is an illustration of a data structure 1200 for arranging calibration data for a given class of detectors 1204, 1206, 1208. The calibration is arranged by detectors 1202 and one can further divide the class of detectors 1202 into the different type of detectors (1204 . . . 1208). The calibration data is further arranged by system independent calibration data 1210 and system dependent calibration data 1212. The reason for this distinction is that the system independent calibration can be run once and stored and only the system dependent calibration need to be run every time.

CONCLUSION

Although specific embodiments have been illustrated and described herein, it will be appreciated by those of ordinary skill in the art that any arrangement which is calculated to achieve the same purpose can be substituted for the specific embodiments shown. This application is intended to cover any adaptations or variations. For example, although described in procedural terms, one of ordinary skill in the art will appreciate that implementations can be made in an object-oriented design environment or any other design environment that provides the required relationships.

In particular, one of skill in the art will readily appreciate that the names of the methods and apparatus are not intended to limit embodiments. Furthermore, additional methods and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types.

I claim:

1. A method for hot swapping a portable detector to an imaging system, the method comprising:
   detecting attachment of the portable detector to the imaging system, wherein the portable detector is operable to be identified by a unique identifier;
   selecting imaging system specific calibration data for the portable detector; and
   integrating the portable detector and the selected calibration data to the operation of the imaging system.

2. The method of claim 1, wherein selecting calibration data for the portable detector further comprises one of:
   reading at least one calibration data stored in the portable detector;
   reading the unique identifier and the calibration data stored in the portable detector; and
   looking up the calibration data for the portable detector stored in the imaging system.

3. The method of claim 2 further comprising:
   interchanging information between the portable detector and the imaging system to initialize the communication channels of the portable detector and the imaging system.

4. The method of claim 1, wherein the portable detector further comprise one of X-ray, ultrasound, or patient monitoring device.

5. The method of claim 1, wherein the unique identifier is an identifier marker added to the portable detector at the time of calibration, an identifier embedded in the portable detector's programmable read-only memory or read only memory, or a media access control address.

6. The method of claim 1, wherein attachment of the portable detector to the imaging system further comprises one of:
   docking the portable detector in the imaging system; and
   electrically coupling the portable detector to the imaging system.

7. The method of claim 1, wherein the calibration data is organized as imaging system dependent calibration data and imaging system independent calibration data.

8. An imaging system comprising:
   a processor;
   a storage device coupled to the processor;
   software means operative on the processor for:
   detecting attachment of a portable detector to the imaging system, wherein the portable detector is identified by a unique identifier;
   selecting imaging system specific calibration data for the portable detector; and,
   integrating the portable detector and the selected calibration data to the operation of the imaging system.

9. The system of claim 8, wherein selecting calibration data for the portable detector further comprises one of:
   reading calibration data stored in the portable detector;
   reading the unique identifier and the calibration data stored in the portable detector; and
   looking up the calibration data for the portable detector stored in the imaging system.

10. The system of claim 9, the system further comprising:
    communication device for interchanging information between the portable detector and the imaging system to initialize the communication channels of the portable detector and the imaging system.

11. The system of claim 8, wherein the portable detector further comprises one of X-ray, ultrasound, or patient monitoring device.

12. The system of claim 8, wherein the unique identifier further comprises an identifier marker added to the portable detector at the time of calibration, an identifier embedded in the portable detector's programmable read-only memory or read only memory, media access control address.

13. The system of claim 8, wherein attachment of the portable detector to the imaging system further comprise one of:
   docking the portable detector in the imaging system; and
   electrically coupling the portable detector to the imaging system.

14. The system of claim 8, wherein the calibration data is organized as imaging system dependent calibration data and imaging system independent calibration data.

15. A computer-accessible medium having executable instructions for integrating a portable detector to an imaging system, the executable instructions capable of directing a processor to perform:
   detecting attachment of a portable detector to the imaging system, wherein the portable detector is identified by a unique identifier;
   interchanging information between the detected attached portable detector and the imaging system to initialize the communication channels of the portable detector and the imaging system;
   selecting imaging system specific calibration data for the portable detector; and,
   integrating the portable detector and the selected calibration data to the operation of the imaging system.

16. The method of claim 15, wherein selecting calibration data for the portable detector further comprises one or more reading calibration data stored in the portable detector, reading the unique identifier and the calibration data stored in the portable detector, or looking up the calibration data for the portable detector stored in the imaging system.

17. The method of claim 15, wherein the portable detector is one of X-ray, ultrasound, or patient monitoring device.

18. The method of claim 15, wherein the unique identifier further comprises an identifier marker added to the portable detector at the time of calibration, an identifier embedded in the portable detector's programmable read-only memory or read only memory, media access control address.

19. The method of claim 15, wherein attachment of the portable detector to the imaging system further comprises one of:
   one of docking the portable detector in the imaging system; and
   electrically coupling the portable detector to the imaging system.

20. The method of claim 15, wherein the calibration data is organized as imaging system dependent calibration data and imaging system independent calibration data.

* * * * *